(12) United States Patent
Tsai

(10) Patent No.: US 10,201,693 B2
(45) Date of Patent: Feb. 12, 2019

(54) CLOSED MALE LUER

(71) Applicant: Hsi-Chin Tsai, New Taipei (TW)

(72) Inventor: Hsi-Chin Tsai, New Taipei (TW)

( * ) Notice: Subject to any disclaimer, the term of this patent is extended or adjusted under 35 U.S.C. 154(b) by 125 days.

(21) Appl. No.: 14/820,004

(22) Filed: Aug. 6, 2015

(65) Prior Publication Data

US 2017/0036008 A1 Feb. 9, 2017

(51) Int. Cl.
*A61M 39/10* (2006.01)

(52) U.S. Cl.
CPC . *A61M 39/1011* (2013.01); *A61M 2039/1033* (2013.01); *A61M 2039/1061* (2013.01); *A61M 2039/1077* (2013.01)

(58) Field of Classification Search
CPC ............. A61M 39/1011; A61M 39/10; A61M 2039/1038; A61M 2039/1077; A61M 2039/1088; A61M 2039/1061; A61M 2039/1005; A61M 2039/1027; A61M 2039/1033; A61M 2039/1044; A61M 2039/267; A61M 2039/268; A61M 39/26; A61M 39/1055; F16D 9/06; F16D 7/048; F16D 7/04; F16D 7/10; F16D 7/044; F16D 7/042; F16D 7/046; F16D 43/2028; F16D 43/202; F16D 43/2022; F16D 43/2024; F16D 43/2026; F16D 43/208
See application file for complete search history.

(56) References Cited

U.S. PATENT DOCUMENTS

| | | | |
|---|---|---|---|
| 2012/0022457 A1* | 1/2012 | Silver | A61M 39/1011 604/187 |
| 2012/0041391 A1* | 2/2012 | Fangrow | A61M 39/1011 604/246 |
| 2012/0153613 A1* | 6/2012 | Kauppi | A61M 16/0816 285/374 |
| 2013/0187381 A1* | 7/2013 | Guala | A61M 39/10 285/387 |
| 2014/0265312 A1* | 9/2014 | McAlister | F16L 19/0231 285/305 |

FOREIGN PATENT DOCUMENTS

EP 1747797 A1 * 1/2007 ............ A61M 39/10

* cited by examiner

*Primary Examiner* — Kami A Bosworth
*Assistant Examiner* — Alexandra Lalonde
(74) *Attorney, Agent, or Firm* — Rabin & Berdo, P.C.

(57) ABSTRACT

A closed male luer includes a first connector having an upper end portion defining an axial recess, an inner circumferential slide track and several first ratchet teeth; and a second connector having lower end portion received in the axial recess of the first connector, having several second ratchet teeth selectively meshed with the first ratchet teeth such that rotation of the first connector in a first direction drives the second connector to rotate simultaneously in the first direction, wherein, after an upper end portion of the second connector is connected with a second member, rotation of the first connector in the first direction or rotation of the second connector in a second direction opposite to the first direction can break up the second ratchet teeth into pieces by the first ratchet teeth, hence permitting the second connector to rotate freely in 360° relative to the first connector.

4 Claims, 12 Drawing Sheets

CLOSED MALE LUER

BACKGROUND OF THE INVENTION

1. Field of the Invention

The present invention relates generally to a closed male luer, more particularly to a closed male luer, similar to a Luer taper connection, for use in medical instruments and laboratory.

2. The Prior Arts

The Luer taper connection is a standardized system of small-scale fluid fittings used for making leak-free connections between a male-taper fitting and its mating female part such that the male-taper fitting and its mating female part can be rotated or loosen relative to each other. This Luer taper connection is generally used in medical instruments, including hypodermic syringe tips, drop sets and fluid transfusion sets for transfer of medical solution into patient bodies.

However, the conventional Luer taper connection has a problem that undesired leakage of hazardous liquid medicine often happens during the entire safe handling continuum in hospital.

Sometimes, where there is limited space and in case the connecting tubing of female part is twisted relative to the male-tapering fitting, which hinders the smooth transfusion of medical solution. At this time, the connecting tubing of female part needs rotation relative to the male-tapering fitting in order to straighten the twist and it is very fastidious to do the straightening. There is also the problem of medicine leakage.

SUMMARY OF THE INVENTION

A primary objective of the present invention is to provide a closed male luer for use in medical instruments (like hypodermic syringe), in which a plurality of first ratchet teeth are meshed selectively with a plurality of second ratchet teeth such that upon rotation of a first connector relative to a second connector in a first direction drives the second connector in the first direction, thereby preventing disengagement of the second connector from a second member which is connected threadedly with the second connector. Once the second member is connected threadedly with the second connector, rotation of the first connector relative to the second connector in the first direction or rotation of the second connector in a second direction opposite to the first direction can break the plurality of second ratchet teeth into pieces such that the second connector can rotate in 360° relative to the first connector by virtue of circumferential slide channel and circumferential slide track so that the second member serving as transfusion tubing can be straightened in a straight line to facilitate smooth transfusion in addition to preventing disengagement of the second connector with the second member.

The closed male luer of the present invention is used for interconnecting first and second members, accordingly includes a first connector and a second connector.

The first connector has upper and lower end portions. The upper end portion has an inner peripheral wall that defines an axial recess and that is formed with a plurality of first ratchet teeth. The lower end portion of the first connector is adapted to be connected with the first member.

The second connector is disposed above and in alignment with the first connector. The second connector has upper and lower end portions and an intermediate portion between the upper and lower end portions of the second connector. The lower end portion of the second connector is received in the axial recess of the first connector, has a plurality of second ratchet teeth selectively meshed with the plurality of first ratchet teeth of the first connector such that rotation of the first connector in a first direction drives the second connector to rotate simultaneously in the first direction. The upper end portion of the second connector is adapted to be connected threadedly with the second member. The intermediate portion has an outer peripheral wall defining an outer diameter greater than outer diameters of the upper and lower end portions of the second connector. One of the intermediate portion and the upper end portion of the first connector is formed with a circumferential slide channel and the other one of the intermediate portion and the upper end portion of the first connector is formed with a circumferential slide track and vice versa. After the upper end portion of the second connector is connected threadedly with the second member, rotation of the first connector in the first direction or rotation of the second connector in a second direction opposite to the first direction results in breakage of said plurality of second ratchet teeth done by the plurality of first ratchet teeth, hence permitting the second connector to rotate in 360° relative to the first connector by virtue of the circumferential slide channel and the circumferential slide track.

In one embodiment of the present invention, the circumferential slide track is formed on the inner peripheral wall of the upper end portion of the first connector with the plurality of first ratchet teeth being located above the circumferential slide track. The circumferential slide channel is formed on the outer peripheral wall of the intermediate portion of the second connector.

Preferably, the number of the plurality of second ratchet teeth is less than that of the plurality of first ratchet teeth.

More preferably, the plurality of first ratchet teeth are formed angularly in the inner peripheral wall of the upper end portion of the first connector while the lower end portion of the second connector has an outer peripheral wall formed with the plurality of second ratchet teeth.

In one embodiment, the axial recess of the upper end portion of the first connector has a bottommost surface formed with the plurality of first ratchet teeth while the plurality of second ratchet teeth are formed around a bottom end of an outer peripheral wall of the lower end portion of the second connector.

In one embodiment, the lower end portion of the second connector is dented inwardly and axially so as to form an axial insert hole. The axial recess of the upper end portion of the first connector has a bottommost surface from which an insert tube projects upwardly and axially into the axial insert hole of the second connector so as to define a washer-reception space therebetween. The insert tube has a large-diameter tube section seated on the bottommost surface of the axial recess and a small-diameter section distal from the bottommost surface of the axial recess. The closed male luer of the present invention further includes a washer having a tubular portion sleeved around the small-diameter section of the insert tube and an annular flange extending outwardly and radially from the tubular portion and received fittingly in the washer-reception space, thereby providing leak-free effect between the first connector and the second connector.

One distinct feature of the present invention resides in that the first connector drives the second connector to rotate only in the first direction. Hence, once the second connected is connected threadedly with the second member, rotation of the second connector in a second direction opposite to the first direction cannot result in disengagement of the second connector relative to the second member, thereby providing leak-free effects between the second connector and the second member. In addition, after the plurality of second ratchet teeth are damaged or broken, the second connector can rotate in 360° relative to the first connector by virtue of the circumferential slide channel and the circumferential slide track such that the second member serving as transfusion tubing can be straightened into a straight line from a twisted position while the second connector maintains its threaded engagement with the second member and at the same time engagement between the second and first connectors is not disturbed owing to slight axial movement of the second connector relative to the first connector.

BRIEF DESCRIPTION OF THE DRAWINGS

The present invention will be apparent to those skilled in the art by reading the following detailed description of a preferred embodiment thereof, with reference to the attached drawings, in which.

DETAILED DESCRIPTION OF THE PREFERRED EMBODIMENTS

The accompanying drawings are included to provide a further understanding of the invention, and are incorporated in and constitute a part of this specification. The drawings illustrate embodiments of the invention and, together with the description, serve to explain the principles of the invention.

Figure 1:
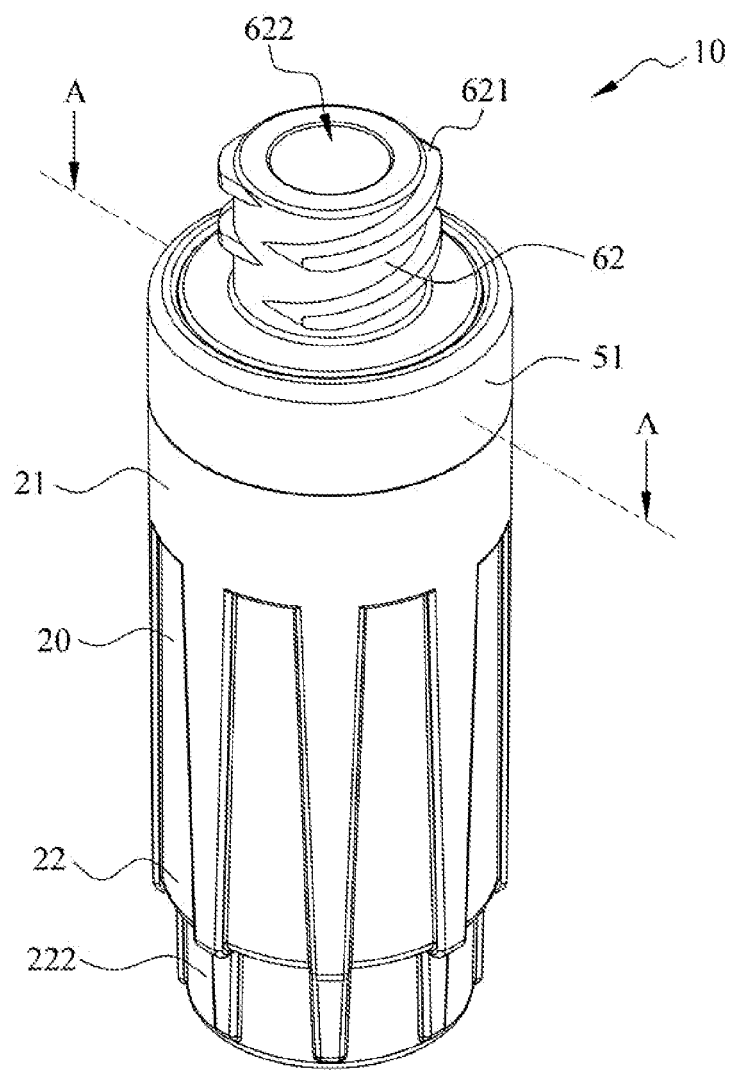
FIG. 1 is a perspective view of a closed male luer of the present invention for interconnecting a first member and a second member.
Figure 2:
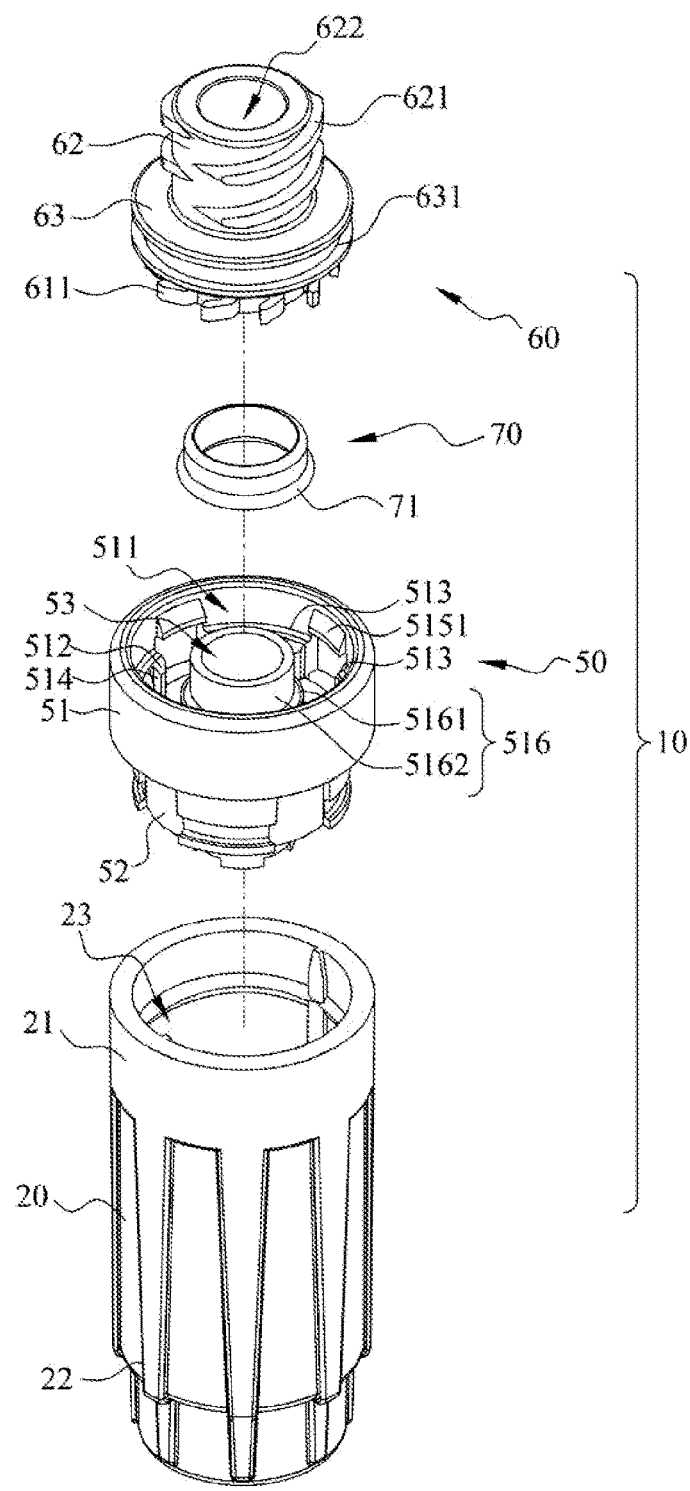
FIG. 2 shows a perspective and exploded view of the first embodiment of the closed male luer of the present invention shown together with the first member.
Figure 3:
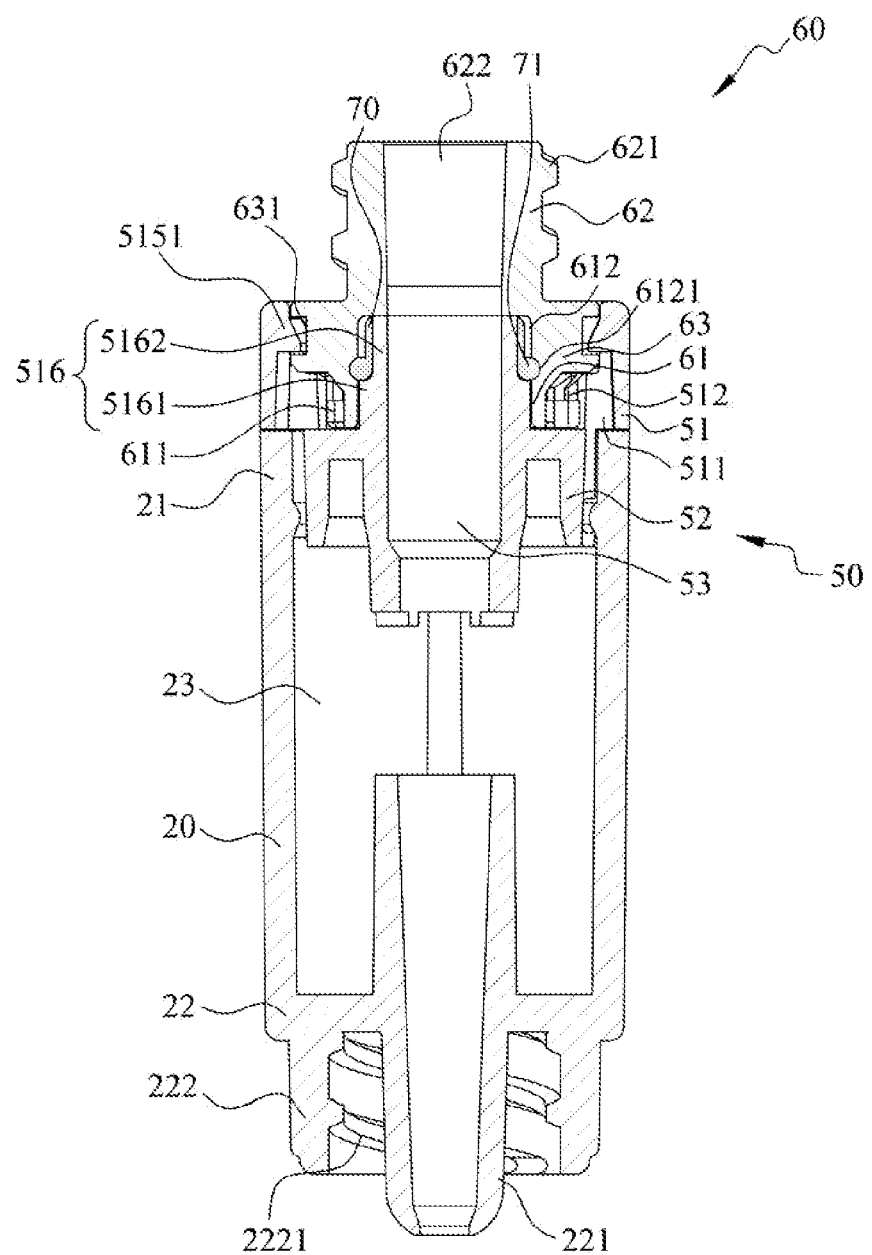
FIG. 3 shows a sectional view of the first embodiment of the closed male luer of the present invention together with the first member.
Figure 4:
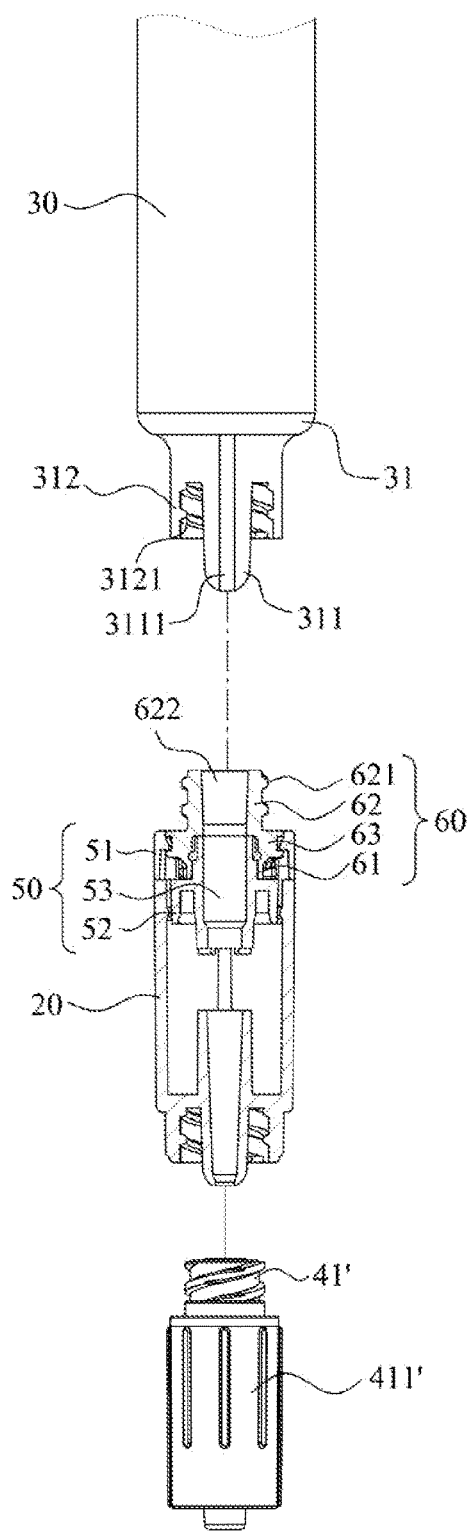
FIG. 4 shows a sectional view of the first embodiment of the closed male luer of the present invention together with the first member and the second member, which serves as a syringe unit.
Figure 5:
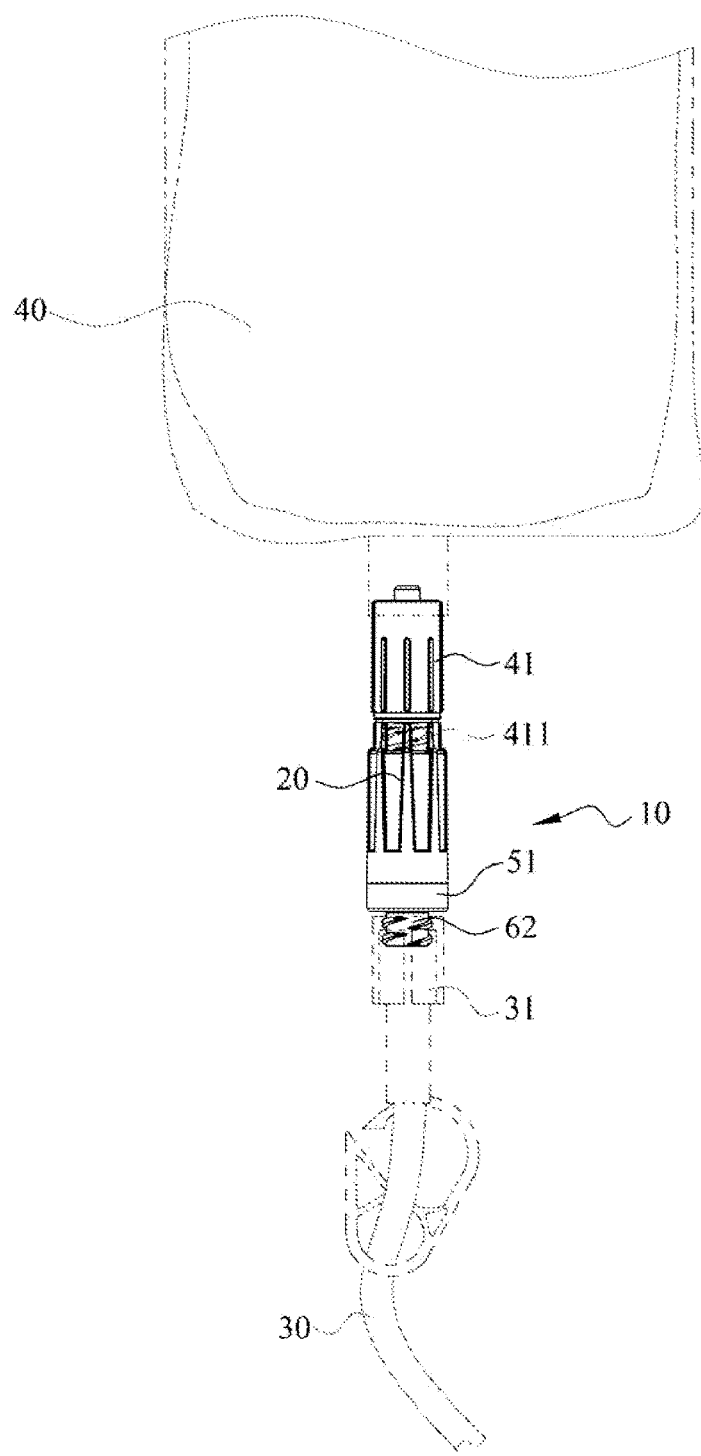
FIG. 5 shows the first embodiment of the closed male luer of the present invention together with the first member and the second member, wherein the first member serves a medical solution bag while the second member serves as a fluid transfusion tubing.

Referring to FIGS. 1-5, FIG. 1 is a perspective view of a closed male luer of the present invention for interconnecting a first member and a second member; FIG. 2 shows a perspective and exploded view of the first embodiment of the closed male luer of the present invention shown together with the first member; FIG. 3 shows a sectional view of the first embodiment of the closed male luer of the present invention together with the first member; FIG. 4 shows a sectional view of the first embodiment of the closed male luer of the present invention together with the first member and the second member, which serves as a syringe unit; and FIG. 5 shows the first embodiment of the closed male luer of the present invention together with the first member and the second member, wherein the first member serves a medical solution bag while the second member serves as a fluid transfusion tubing. As illustrated, the closed male luer 10 of the present invention is used for interconnecting a tubular first member 20 and a tubular second member 30, includes a first connector 50, a second connector 60 disposed above and in alignment with the first connector 50 and a washer 70. The first member 20 has upper and lower end portions 21, 22 and a peripheral wall interconnecting the upper and lower end portions 21, 22 of the first member 20 to define a chamber 23 therein. The lower end portion 22 of the first member 20 has a male-connection head 221 projecting axially and outwardly therefrom and a circular flange 222 that surrounds male-connection head 221 and that is formed with internal threads 2221 such that the male-connection head 221 is exposed from the circular flange 222. The second member 30 has a lower end portion 31 and a male-connection head 311 that projects axially and outwardly therefrom and that defines an axial passage 3111, and a circular flange 312 that surrounds male-connection head 311 and that is formed with internal threads 3121 such that the male-connection head 311 is exposed from the circular flange 312. Note that the second member 30 can serve as a syringe barrel and the inner threads 2221 of the first member 20 is connected threaded to a female part 411' of a needlefree connector 41' as best shown in FIG. 4 or the inner threads 2221 of the first member 20 is connected threaded to a female part 411 of a needlefree connector 41 of a medical solution bag 40 or else the second member 30 serves a transfusion tubing, as best shown in FIG. 5. Alternately, the first member 20 can be connected to a dropping bottle or a medical solution bag.

The first connector 50 has upper and lower end portions 51, 52. The upper end portion 51 of the first connector 50 has an inner peripheral wall that defines an axial recess 511 and that is formed with a plurality of first ratchet teeth 512. In other words, the plurality of first ratchet teeth 512 projects radially toward an axis of the recess 511 of the upper end portion 51 of the first connector 50. Preferably, a circumferential slide track is formed on the inner peripheral wall of the upper end portion 51 of the first connector 50 with the plurality of first ratchet teeth 512 being located below the circumferential slide track. To be more specific, the circumferential slide track of the upper end portion 51 of the first connector 50 is constituted by a plurality of angularly spaced apart blocks 5151. The plurality of first ratchet teeth 512 are divided into several sets 513 such that each set is constituted by three first ratchet teeth 512 and the several sets 513 are angularly spaced in the inner peripheral wall and that each of the plurality of angularly spaced apart blocks 5151 is located above and between an adjacent pair of the first ratchet teeth sets 513. In other words, each block 5151 is staggered with respect to each set of the first ratchet teeth 512. The axial recess 511 of the upper end portion 51 of the first connector 50 has a bottommost surface from which an insert tube 516 projects upwardly and axially. The insert tube 516 has a large-diameter tube section 5161 seated on the bottommost surface of the axial recess 511 and a small-diameter section 5162 distal from the bottommost surface of the axial recess 511. Note the upper end portion 51 of the first connector 50 has an outer diameter greater than that of the lower end portion 52 of the first connector 50. In the embodiment, the outer diameter of the upper end portion 51 of the first connector 50 is equivalent to that of the upper end portion 21 of the first member 20 such that the lower end portion 52 of the first connector 50 can be inserted into and abuts against the upper end portion 21 of the first member 20, wherein the first connector 50 defines a first axial passage 53 in spatial communication with the insert tube 516 of the upper end portion 51 and the chamber 23 in the first member 20.

The second connector 60 has upper and lower end portions 62, 61, and an intermediate portion 63 between the upper and lower end portions 62, 61 of the second connector 60. The lower end portion 61 of the second connector 60 is received in the axial recess 511 of the first connector 50, has a plurality of second ratchet teeth 611. To be more specific, the lower end portion 61 of the second connector 60 has an outer peripheral wall formed with the plurality of second ratchet teeth 611. In other words, the ratchet teeth 611 extend outwardly and radially in a direction away from an axis of the lower end portion 61 of the second connector 60. In fact, the lower end portion 61 of the second connector 60 serves as a ratchet wheel in this embodiment such that the plurality of second ratchet teeth 611 are selectively meshed with the plurality of first ratchet teeth 512 of the first connector 50 owing to the number of the plurality of second ratchet teeth 611 is less than that of the plurality of first ratchet teeth 512. The second connector 60 further defines an axial passage 622 extending through the upper and lower end portions 62, 61 of the second connector 60. The intermediate portion 63 has an outer peripheral wall defining an outer diameter greater than outer diameters of the upper and lower end portions 62, 61 of the second connector 60. The intermediate portion 63 is formed with a circumferential slide channel 631. The lower end portion 61 of the second connector 60 is dented inwardly and axially so as to form an axial insert hole 612 such that after the upper end portion 62 of the second connector 60 is connected threadedly with the second member 30 via the outer and inner threads 3121, 621, the insert tube 51 of the first connector 50 extends into the axial insert hole 612 of the second connector 60 so as to define a washer-reception space 6121 therebetween. At this time, the male-connection head 311 of the second member 30 extends into the axial passage 622 of the second connector 60, thereby establishing spatial communication between the axial passage 53 of the first connector 50 and the axial passage 3111 of the second member 30, as best shown in FIG. 4.

The washer 70 is disposed between the first connector 50 and the second connector 60, has a tubular portion sleeved around the small-diameter section 5162 of the insert tube 516 and an annular flange 71 extending outwardly and radially from the tubular portion and seated fittingly in the washer-reception space 6121 (see FIG. 3), thereby providing leak-free effect between the first connector 50 and the second connector 60.

Figure 6:
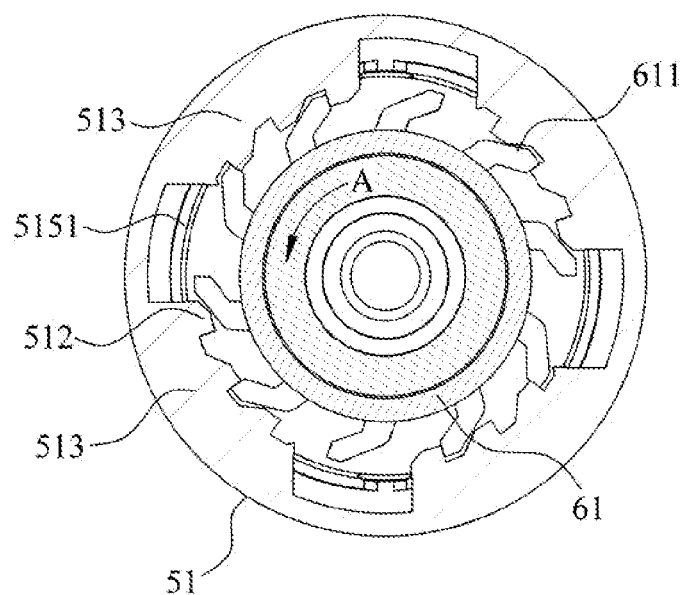
FIG. 6 shows a cross-sectional view of the first embodiment of the closed male luer of the present invention, illustrating how a first connector drives a second connector to rotate in a first direction.

FIG. 6 shows a cross-sectional view of the first embodiment of the closed male luer of the present invention, illustrating how the first connector drives the second connector to rotate in a first direction. After the closed male luer 10 of the present invention is connected threadedly with the second member 30 (when the upper end portion 62 of the second connector 60 is connected threadedly with the second member 30), rotation of the first connector 50 in a first direction A (see FIG. 6) drives the second connector 60 to rotate simultaneously in the first direction because the plurality of first ratchet teeth 512 engage with the plurality of second ratchet teeth 611 in the first direction. In the event, rotation of the first connector 50 relative to the second connector 60 in a second direction B opposite to the first direction A or rotation of the second connector 60 relative to the first connector 50 in the first direction A results in idle rotation of the second connector 60 relative to the first connector 50 since the plurality of first ratchet teeth 512 and the plurality of second ratchet teeth 611 disengage from one another.

Figure 7:
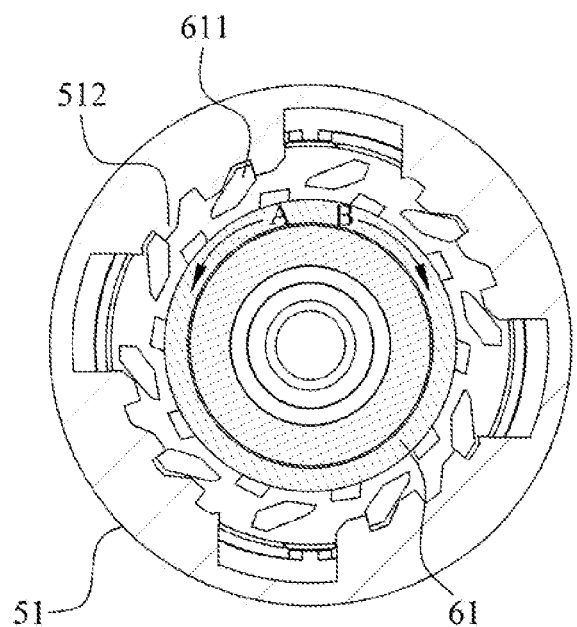
FIG. 7 shows a cross-sectional view of the first embodiment of the closed male luer of the present invention, illustrating how the second connector rotates in 360° relative to the first connector in a second direction opposite to the first connector.

Referring to FIG. 7, when the second member 30 serves as a transfusion tube and after the upper end portion 62 of the second connector 60 is connected threadedly with the lower end portion 31 of the second member 30 and in case there exist a twist between the two units, which in turn, hinders smooth fluid transfusion. At this time, the user can apply a torque on the first connector 50 in the first direction A or rotation of the second connector in the second direction B opposite to the first direction A can breakage up the plurality of second ratchet teeth 611 into pieces by the plurality of first ratchet teeth 512, hence causing the second connector 60 to rotate freely in 360° relative to the first connector 50 in both of the first and second direction along the same plane by virtue of the circumferential slide channel 631 and the circumferential slide track, as best shown in FIG. 7.

Figure 8:
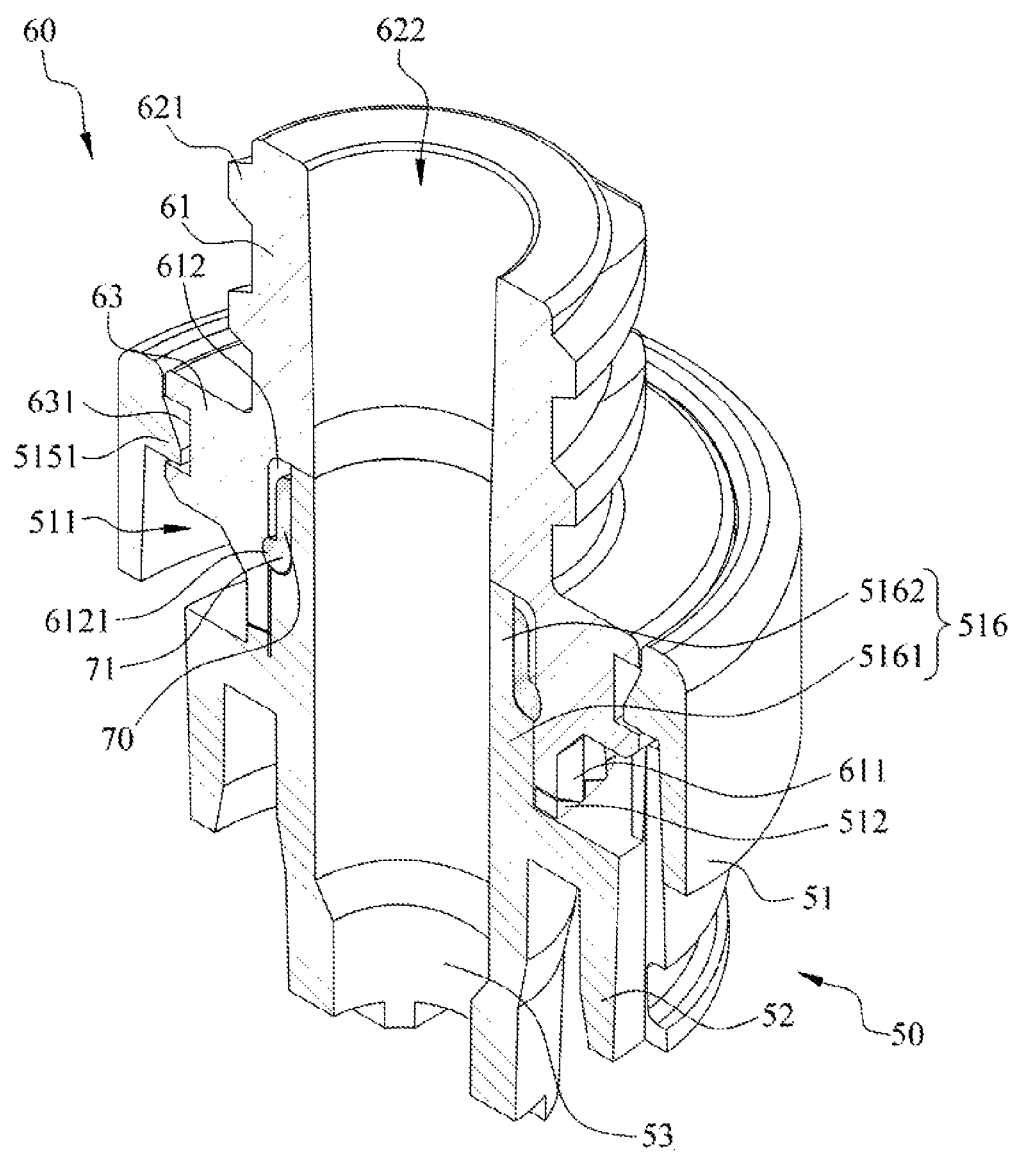
FIG. 8 shows a cross-sectional view of the second embodiment of the closed male luer of the present invention.

FIG. 8 shows a cross-sectional view of the second embodiment of the closed male luer 10 of the present invention and has the structure similar to the first embodiment, except in that the plurality of first ratchet teeth 512 are disposed angularly on the bottommost surface of the axial recess 511 in the upper end portion 51 of the first connector 50 rather than on the inner peripheral wall of the upper end portion 51 of the first connector 50 while the plurality of second ratchet teeth 611 are disposed on the bottom end of the lower end portion 61 of the second connector 60. In other words, the plurality of first ratchet teeth 512 project upwardly from the bottommost surface of the axial recess 511 toward an axis of the upper end portion 51 of the first connector 50 while the plurality of second ratchet teeth 611 project downwardly from the bottom end of the lower end portion 61 of the second connector 60 so as to selectively mesh with the plurality of first ratchet teeth 512.

Figure 9:
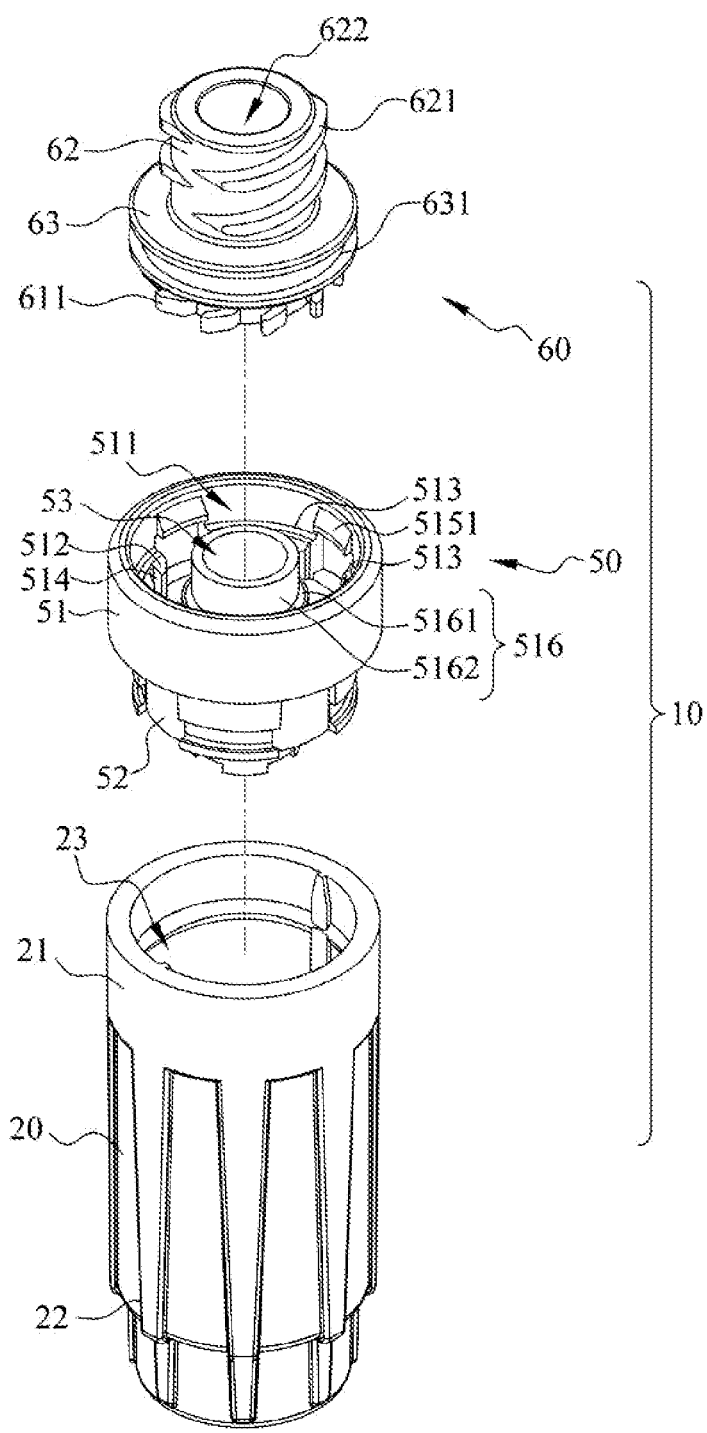
FIG. 9 shows a perspective and exploded view of the third embodiment of the closed male luer of the present invention shown together with the first member.

FIG. 9 shows a perspective and exploded view of the third embodiment of the closed male luer of the present invention shown together with the first member, and has the structure similar to the first embodiment, except in that no washer 70 is applied herein and at the same time the washer-reception space 6121 is excluded owing to the planar surface defining the bottommost surface of the axial insert hole.

Figure 10:
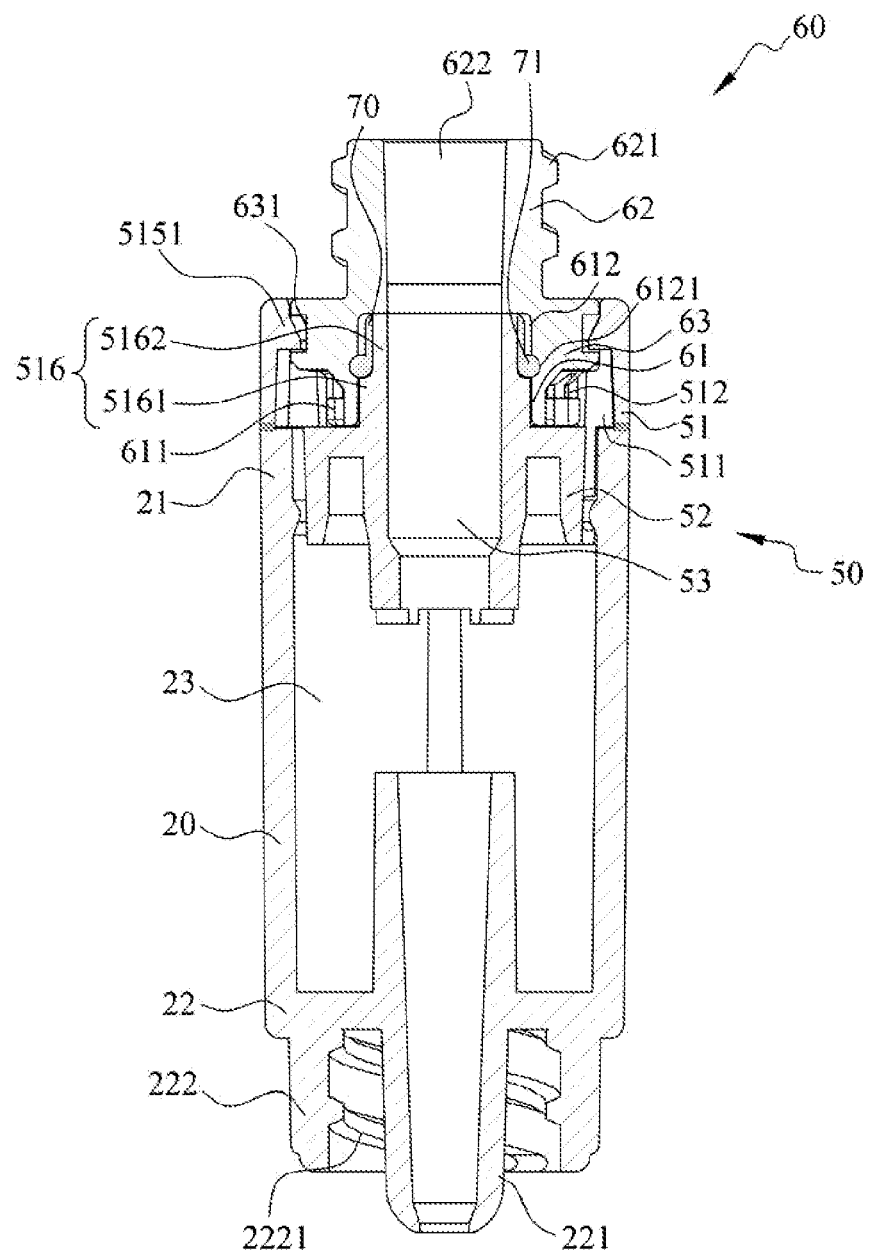
FIG. 10 shows a cross-sectional view of the fourth embodiment of the closed male luer of the present invention.

FIG. 10 shows a cross-sectional view of the fourth embodiment of the closed male luer of the present invention and has the structure similar to the first embodiment, except that the bottom of the upper end portion 51 of the first connector 50 is connected to the upper end portion 21 of the first member 20 via ultrasonic welding or other techniques.

Figure 11:
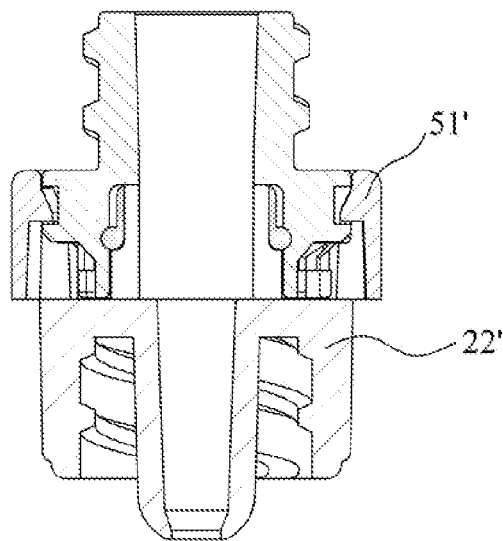
FIG. 11 shows a cross-sectional view of the fifth embodiment of the closed male luer of the present invention.

FIG. 11 shows a cross-sectional view of the fifth embodiment of the closed male luer of the present invention and has the structure similar to the first embodiment, except that the first member 20 and the first connector 50 have different structures respectively. To be more specific, the first member 20 has only the lower end portion 22' while the first connector 50 has only the upper end portion 51' such that the upper end portion 51' of the first connector 50 is directly connected to the lower end portion 22' of the first member 20.

Figure 12:
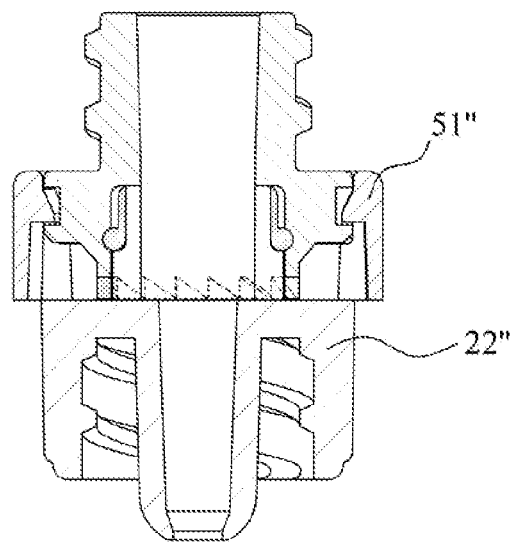
FIG. 12 shows a cross-sectional view of the sixth embodiment of the closed male luer of the present invention.

FIG. 12 shows a cross-sectional view of the sixth embodiment of the closed male luer of the present invention and has the structure similar to the second embodiment, except that the first member 20 and the first connector 50 have different structures respectively. To be more specific, the first member 20 has only the lower end portion 22" while the first connector 50 has only the upper end portion 51" such that the upper end portion 51" of the first connector 50 is directly connected to the lower end portion 22" of the first member 20. At this time, the plurality of first ratchet teeth 512 project upwardly from the bottommost surface of the axial recess towards an axis of the upper end portion 51" of the first connector 50 while the plurality of second ratchet teeth 611 project downwardly from the bottom end of the lower end portion 61 of the second connector 60 so as to selectively mesh with the plurality of first ratchet teeth 512.

One distinct feature of the present invention resides in that since the plurality of first ratchet teeth 512 of the first connector 50 are selectively meshed with the plurality of second ratchet teeth 611 of the second connector 60, rotation of the first connector 50 in the first direction A drives the second connector 60 to rotate in the first direction A only. In other words, the second connector 60 cannot rotate in the second direction B opposite to the first direction A. Under this condition, after the second connector 60 is connected threadedly with the second member 30, the second connector 60 is unable to disengage from the second member 30, thereby providing leak-free effects therebetween. Especially, when transfusing medicine solution from within a syringe unit, drop bottle or medical fluid bag to a patient, the closed male luer 10 of the present invention can prevent the medical staff and the patient's family since no leakage of medicine solution will occur during the transfusion period, thereby ensuring complete transfusion of medicine solution into the patient's body. After use, the closed male luer 10 of the present invention is discarded together with the syringe unit, drop bottle or medical fluid bag into a medical waste bin.

Another distinct feature of the present invention resides in that after the upper end portion 62 of the second connector 60 is connected threadedly with the lower end portion 31 of the second member 30, the user can apply a torque forcibly on the first connector 50 to rotate in the first direction A or on the second connector 60 to rotate in the second direction B results in breakage of the plurality of second ratchet teeth done by the plurality of first ratchet teeth, hence permitting the second connector 60 to rotate in 360° relative to the first connector 50 by virtue of the circumferential slide channel 631 formed on the outer peripheral wall of the intermediation portion of the second connector and the circumferential slide track formed in the inner peripheral wall of the first connector in order to straighten the twist between the second member 30 and the second connector 60 without disturbing the threaded engagement between the two units. Also note that no radial displacement is caused between the first connector 50 and the second connector 60 during 360° rotation of the second connector 60 relative to the first connector 50.

Moreover, since the number of the plurality of second ratchet teeth 611 is less than that of the plurality of first ratchet teeth 512 assists in the breakage of the plurality of second ratchet teeth 611.

Besides, formation of the plurality of angularly spaced apart blocks 5151 in the circumferential slide track of the upper end portion 51 of the first connector 50 economizes the material expense without disturbing the function feature of the circumferential slide track.

Since the plurality of first ratchet teeth 512 are divided into several sets 513 such that each of the plurality of angularly spaced apart blocks 5151 is located above and between an adjacent pair of the sets 513 such that once the lower end portion 61 of the second connector 60 is inserted into the axial recess 51 in the upper end portion 51 of the first connector 50, no disturb is caused to the plurality of second ratchet teeth 611 owing to the empty space formed between adjacent pairs of the plurality of angularly spaced apart blocks 5151.

Note that after the tubular portion of the washer 70 is sleeved around the small-diameter section 5162 of the insert tube 516, the annular flange 71 extending outwardly and radially from the tubular portion and is received fittingly in the washer-reception space 6121, thereby providing leak-free effect between the first connector 50 and the second connector 60.

The present invention helps prevent leaks of hazardous liquid medicine during the entire safe handling continuum in hospital. Upon disconnecting from the female part 411, 411' of the needle free connector 41, 41', the present invention automatically self-seals and closes the flow system, preventing spills from syringes or infusion sets, and also remains closed until it connects with another standard needlefree connector 41, 41'.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A closed male luer for interconnecting a first member and a second member, comprising:
   a first connector having upper and lower end portions, said upper end portion having an inner peripheral wall that defines an axial recess and that is formed angularly with a plurality of first ratchet teeth, each of said plurality of first ratchet teeth having a first vertical surface, a first horizontal surface and a first inclined surface, said first horizontal surface connected between said first vertical surface and said first inclined surface, said first inclined surface being at an angle greater than 90° from said horizontal surface, two adjacent first ratchet teeth spaced apart and formed with a first receiving groove, said lower end portion being adapted to be connected with the first member, a circumferential slide track formed on said inner peripheral wall of said upper end portion of said first connector with said plurality of first ratchet teeth being located below said circumferential slide track; and
   a second connector disposed above and in alignment with said first connector, said second connector having upper and lower end portions, and an intermediate portion between said upper and lower end portions of said second connector, a circumferential slide channel formed on an outer peripheral wall of said intermediate portion of said second connector, said lower end portion of said second connector being received in said axial recess of said first connector, having an outer peripheral wall formed with a plurality of second ratchet teeth, each of said plurality of second ratchet teeth having a base portion and an extension portion, the base portion projecting radially from said outer peripheral wall of the lower end portion of the second connector, and the extension portion extending outwardly and laterally at an obtuse angle from the base portion, the extension portion, in meshing with a corresponding pair of the first ratchet teeth, projecting into said first receiving groove between the corresponding pair of the first ratchet teeth, a wall of said first receiving groove having an angle corresponding to the angle at which the extension portion extends from the base portion, wherein said plurality of second ratchet teeth are selectively meshed with said plurality of first ratchet teeth of said first connector such that rotation of said first connector in a first direction drives said second connector to rotate simultaneously in said first direction, said upper end portion of said second connector being adapted to be connected threadedly with the second member, rotation of said first connector relative to said second connector in a second direction opposite to said first direction or rotation of said second connector relative to said first connector in said first direction resulting in disengagement of said plurality of first ratchet teeth from said plurality of second ratchet teeth and idle rotation of said second connector relative to said first connector, the outer peripheral wall of said intermediate portion of said second connector defining an outer diameter greater than outer diameters of said upper and lower end portions of said second connector;

wherein, a number of said plurality of second ratchet teeth is less than a number of said plurality of first ratchet teeth; and wherein, after said upper end portion of said second connector is connected threadedly to be in threaded engagement with the second member, rotation of the first connector in the first direction or rotation of the second connector in the second direction opposite to the first direction can break up said plurality of second ratchet teeth into pieces by said plurality of first ratchet teeth, hence permitting the second connector to rotate freely in a same plane along both of the first and second directions in 360° relative to the first connector by virtue of the circumferential slide channel and the circumferential slide track such that the second member serving as transfusing tubing can be straightened into a straight line from a twisted position while the second connector maintains the threaded engagement with the second member and at the same time engagement between the second and first connectors is not disturbed owing to slight axial movement of the second connector relative to the first connector.

2. The closed male luer according to claim 1, wherein said circumferential slide track of said upper end portion of said first connector is constituted by a plurality of angularly spaced apart blocks.

3. The closed male luer according to claim 2, wherein said plurality of first ratchet teeth are divided into several sets such that each of said plurality of angularly spaced apart blocks is located above and between an adjacent pair of said sets.

4. The closed male luer according to claim 1, wherein said lower end portion of said second connector is dented inwardly and axially so as to form an axial insert hole, said axial recess of said upper end portion of said first connector having a bottommost surface from which an insert tube projects upwardly and axially into said axial insert hole of said second connector so as to define a washer-reception space therebetween, said insert tube having a large-diameter tube section seated on said bottommost surface of said axial recess and a small-diameter section distal from said bottommost surface of said axial recess, the closed male luer further comprising a washer having a tubular portion sleeved around said small-diameter section of said insert tube and an annular flange extending outwardly and radially from said tubular portion and received fittingly in said washer-reception space, thereby providing leak-free effect between said first connector and said second connectors.

* * * * *